United States Patent [19]

Kawahara et al.

[11] 4,318,886
[45] Mar. 9, 1982

[54] AUTOMATIC HLA TYPING APPARATUS

[75] Inventors: Atsushi Kawahara, Tokyo; Masahiro Sawada, Kawasaki; Norio Fujii, Urawa, all of Japan

[73] Assignee: Nippon Kogaku K.K., Tokyo, Japan

[21] Appl. No.: 206,610

[22] Filed: Nov. 13, 1980

[30] Foreign Application Priority Data

Nov. 19, 1979 [JP] Japan .................................. 54-148794
Dec. 4, 1979 [JP] Japan .................................. 54-156319
Dec. 4, 1979 [JP] Japan .................................. 54-156320
Dec. 4, 1979 [JP] Japan .................................. 54-156321

[51] Int. Cl.³ ...................... G01N 33/80; G01N 33/50
[52] U.S. Cl. .................................. 422/68; 23/230 B; 356/39; 424/12
[58] Field of Search .................. 23/230 B; 356/39; 424/11, 12; 422/50, 68, 67, 73; 364/497; 435/7, 34

[56] References Cited

U.S. PATENT DOCUMENTS

| | | | |
|---|---|---|---|
| 3,824,393 | 7/1974 | Brain | 356/39 X |
| 3,916,205 | 10/1975 | Kleinerman | 356/39 X |
| 3,951,605 | 4/1976 | Natelson | 422/67 X |
| 4,082,457 | 4/1978 | Kohno et al. | 356/39 |
| 4,265,873 | 5/1981 | Sheehy et al. | 424/12 X |
| 4,271,123 | 6/1981 | Curry et al. | 422/67 X |

*Primary Examiner*—Ronald Serwin
*Attorney, Agent, or Firm*—Shapiro and Shapiro

[57] ABSTRACT

Apparatus for automatically typing HLA (Human Leukocyte Antigen) is disclosed. An optical image of a sample containing lymphocytes is formed by a phase-contrast microscope. The optical image is transformed into electrical picture signal through a image pick-up unit which in turn is transformed into binary picture patterns for a predetermined area site in the image through a window circuit. The obtained binary picture patterns are compared with template patterns of predetermined features corresponding to reacted and non-reacted lymphocyte images to detect and type the lymphocyte image. With this typing apparatus, HLA typing test can be conducted automatically with high accuracy.

1 Claim, 72 Drawing Figures

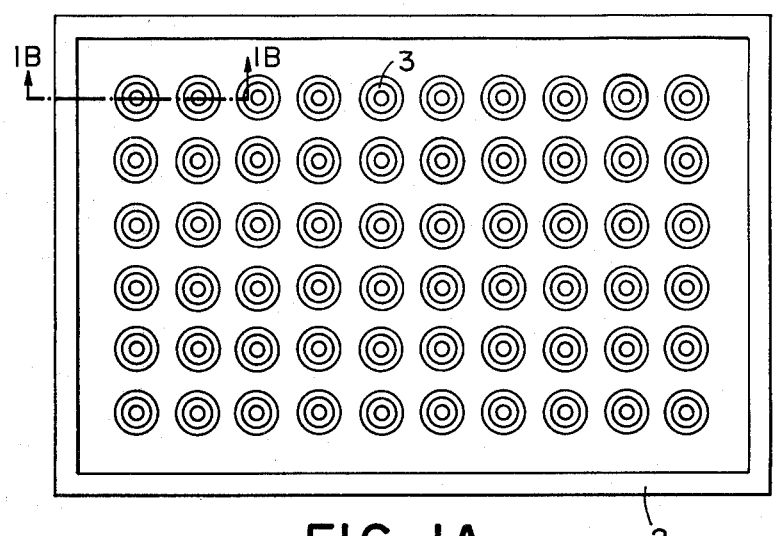
FIG. IA
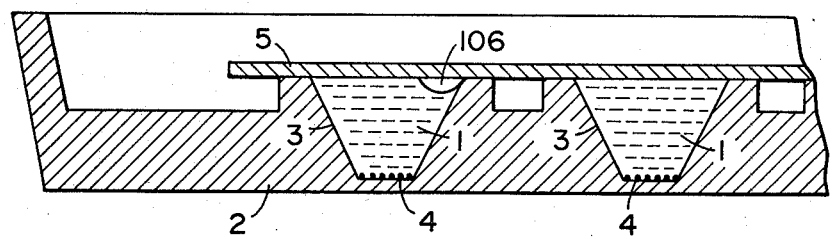
FIG. IB
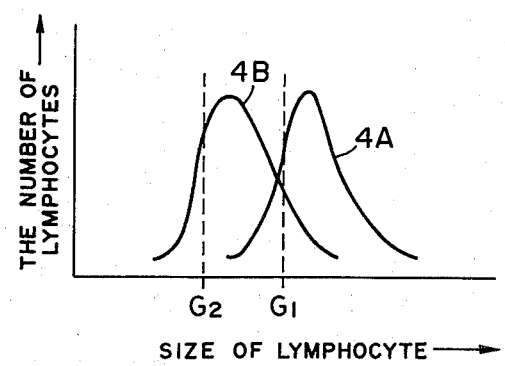
FIG. 2

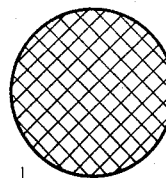
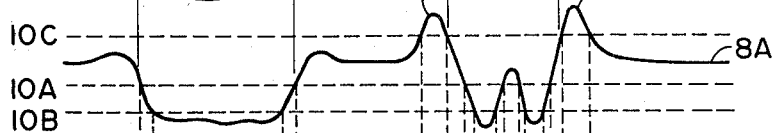
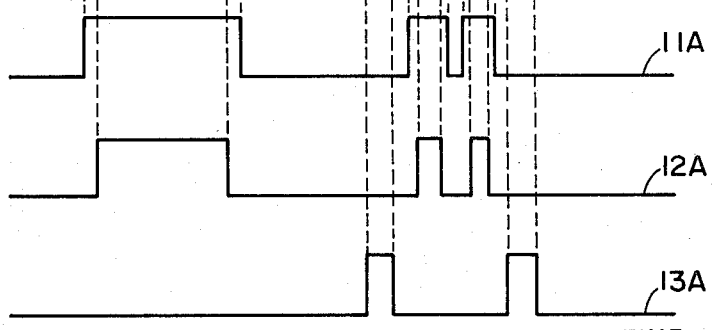
FIG. 4A
FIG. 4B
FIG. 4C
FIG. 4D
FIG. 4E
FIG. 5
FIG. 6
FIG. 7A  FIG. 7B
FIG. 8  FIG. 9

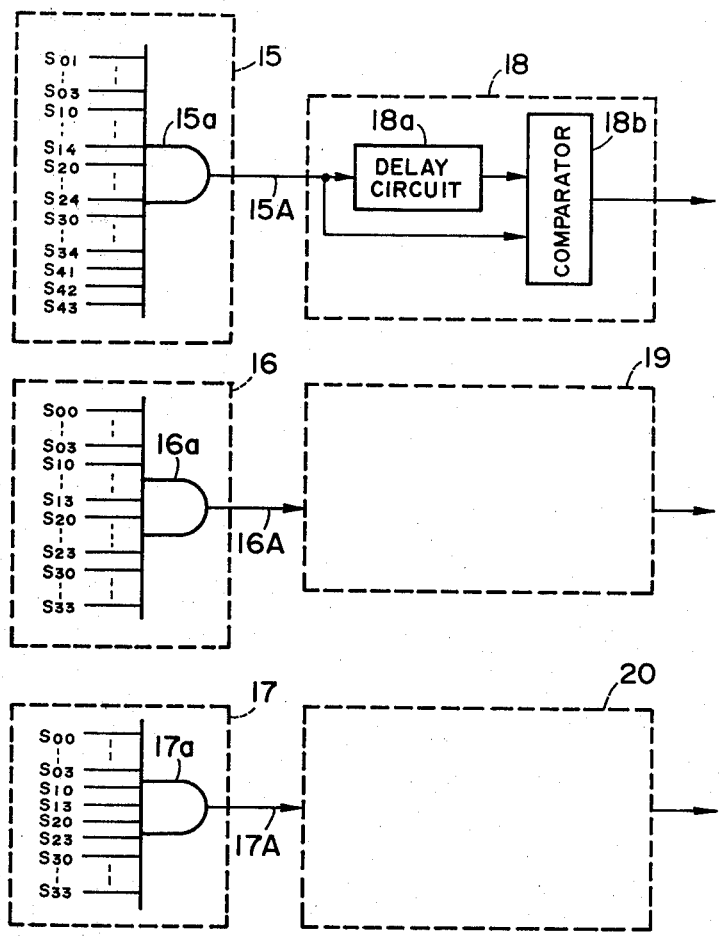
FIG. 13
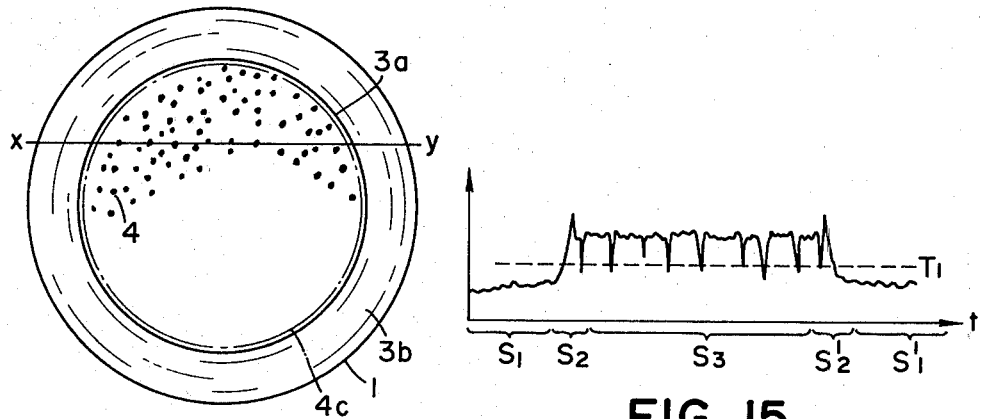
FIG. 14
FIG. 15

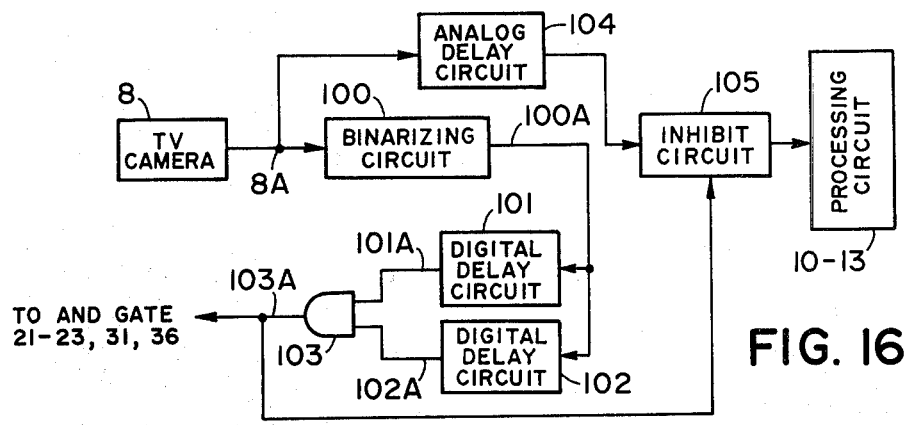
FIG. 16
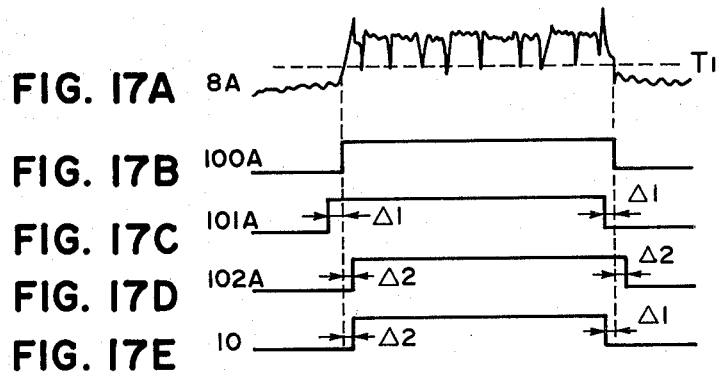
FIG. 17A 8A
FIG. 17B 100A
FIG. 17C 101A
FIG. 17D 102A
FIG. 17E 10
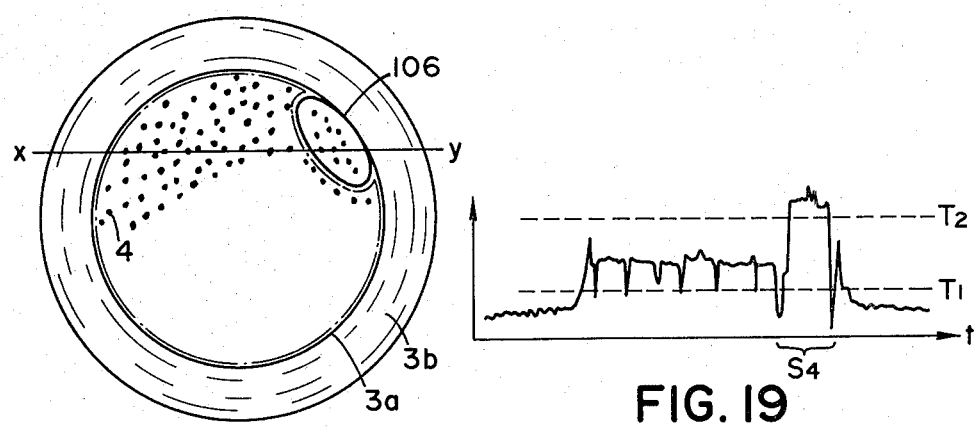
FIG. 18
FIG. 19

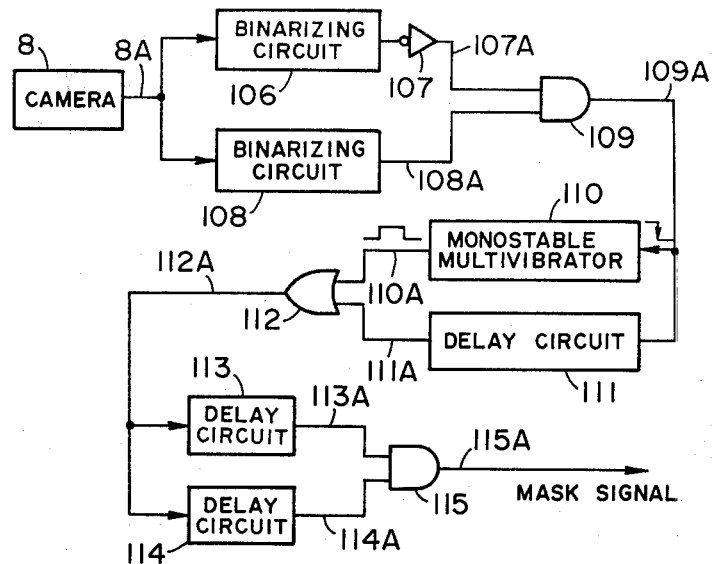
FIG. 20
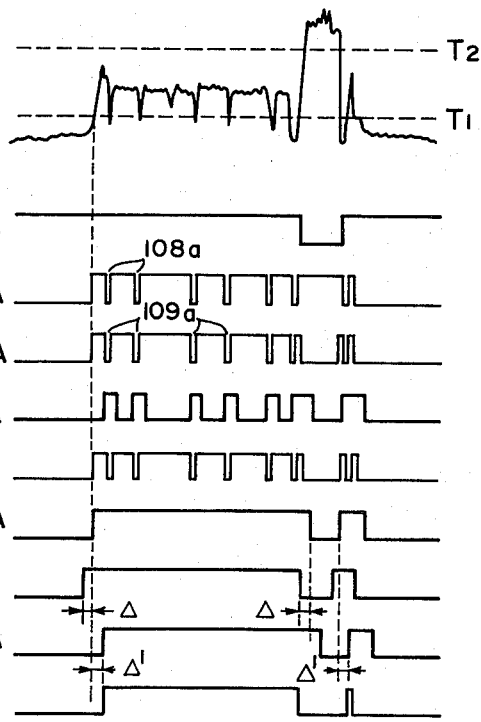
FIG. 21A 8A
FIG. 21B 107A
FIG. 21C 108A
FIG. 21D 109A
FIG. 21E 110A
FIG. 21F 111A
FIG. 21G 112A
FIG. 21H 113A
FIG. 21I 114A
FIG. 21J 115A

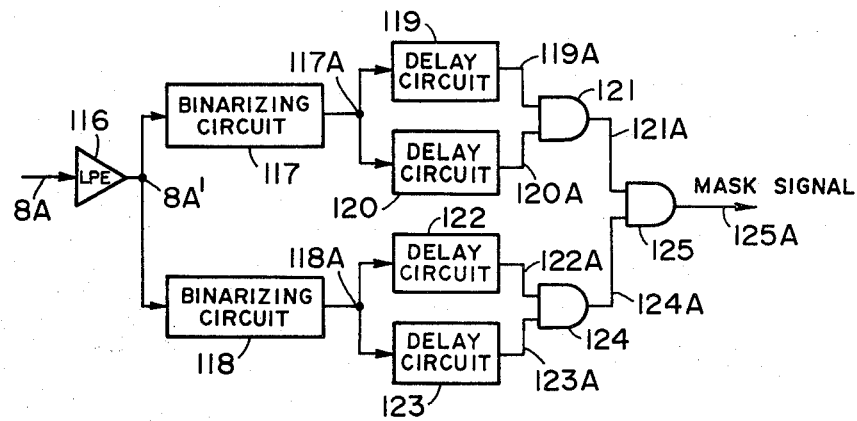
FIG. 22
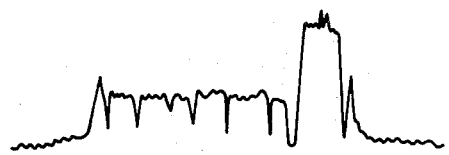
FIG. 23A  8A
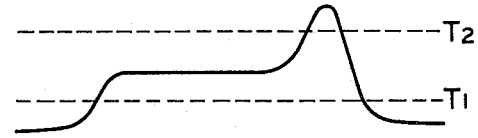
FIG. 23B  8A'

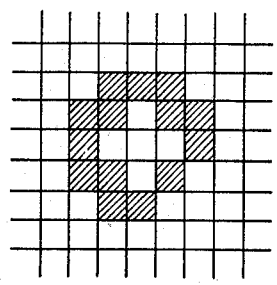
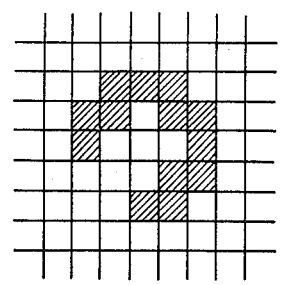
FIG. 24A  FIG. 24B
  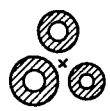 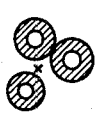
FIG. 25A  FIG. 25B  FIG. 25C  FIG. 25D
| A | $S_{11}$ | $S_0$ | $S_1$ | A |
|---|---|---|---|---|
| $S_{10}$ | $H_7$ | $H_0$ | $H_1$ | $S_2$ |
| $S_9$ | $H_6$ | C | $H_2$ | $S_3$ |
| $S_8$ | $H_5$ | $H_4$ | $H_3$ | $S_4$ |
| A | $S_7$ | $S_6$ | $S_5$ | A |
FIG. 26
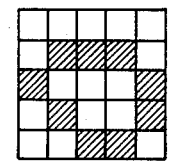 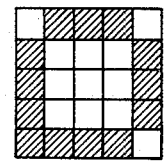
FIG. 27A  FIG. 27B
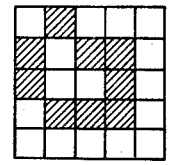
FIG. 27C
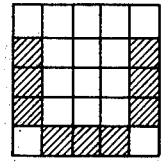 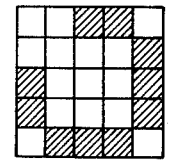
FIG. 28A  FIG. 28B

AUTOMATIC HLA TYPING APPARATUS

BACKGROUND OF THE INVENTION

1. Field of the Invention

The present invention relates to apparatus for automatically typing HLA (Human Leukocyte Antigen).

2. Description of the Prior Art

The typical conventional procedure of HLA typing test is as follows:

At first, lymphocytes in human leukocyte are reacted with a group of HLA antisera. After adding a complement, eosin is added to the reaction mixture. The examiner observes the resultant of the reaction through a phasecontrast microscope and visually calculates the number of reacted positive lymphocytes and that of non-reacted negative lymphocytes to know the ratio of the former to the latter. Based on the calculations, the examiner estimates the ratio of the number of positive lymphocytes to the total number of lymphocytes in the sample, that is, the positivity of the sample by which the type of HLA of the sample is determined.

Of course, the above procedure of HLA typing test requires not only a long time but also high skillfulness. Automation in HLA typing has been desired for a long time. Such HLA typing test has been conducted in a time consuming manner and a very high level of skillfulness has been required therefor.

SUMMARY OF THE INVENTION

It is therefore the primary object of the invention to provide an automated HLA typing apparatus which enables to conduct HLA typing test automatically with high accuracy.

Other and further objects, features and advantages of the invention will appear more fully from the following description of preferred embodiments with reference to the accompanying drawings.

BRIEF DESCRIPTION OF DRAWINGS

FIGS. 1A and 1B show a microtest plate in plan view and cross sectional view respectively;

FIG. 2 is a graph showing the distribution of non-annular lymphocytes;

FIG. 4 shows waveforms of the outputs in the circuit shown in FIG. 3;

FIG. 5 is a block diagram showing a concrete form of the window circuit;

FIG. 6 shows an example of 5 by 5 window;

FIGS. 7 through 9 show template patterns of pattern metching circuits;

FIG. 13 is a block diagram showing a concrete form of pattern metching circuit and end point detector together;

FIG. 14 is a plan view of a microscopic image of a well;

FIG. 15 is a waveform of picture signal of the microscopic image obtained by a certain scanning line;

FIG. 16 shows a concrete form of mask signal generator;

FIG. 17 is a timing chart of signals of FIG. 16;

FIGS. 18 and 19 are views similar to FIGS. 14 and 15 respectively;

FIGS. 20 and 21 are views similar to FIGS. 16 and 17 respectively;

FIGS. 22 and 23 are views similar to FIGS. 16 and 17 respectively;

FIG. 24 is a plan view of binary images of negative lymphocytes;

FIG. 25 is a schematic view showing states of densely gathering lymphocytes;

FIG. 26 shows a 5×5 pixel area;

FIGS. 27 and 28 show the templates for detecting annular negative lymphocytes;

DESCRIPTION OF PREFERRED EMBODIMENTS

Figure 3:
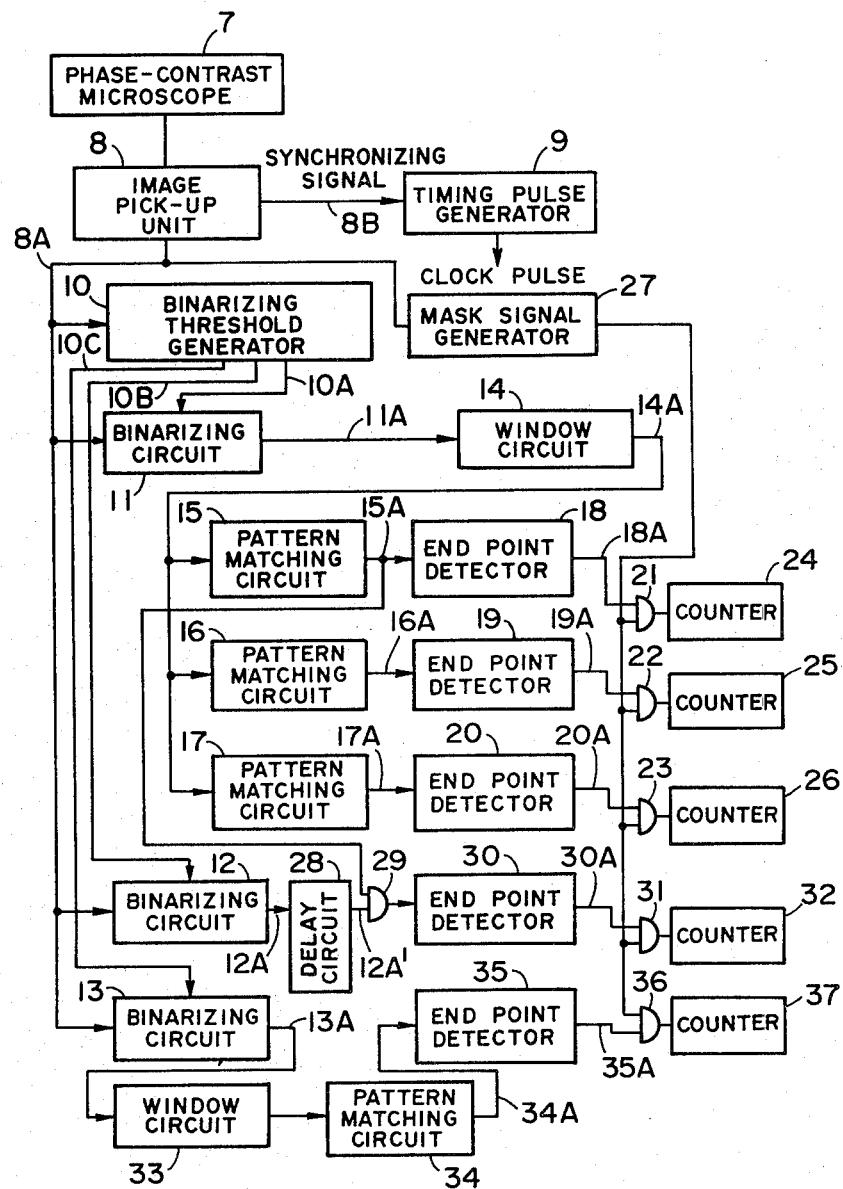
FIG. 3 is a block diagram of an embodiment of the present invention.

Referring first to FIGS. 1A and 1B, reference numeral 1 designates a liquid sample for which a HLA examination is to be conducted. The sample 1 is poured into wells 3 of a microtest plate, that is, a Terasaki plate 2. Lymphocytes 4 in the sample settle on the bottoms of the wells 3. The wells are covered with a cover glass 5. The microtest plate 2 with the HLA test sample is placed on the stage of a phase-contrast microscope (not shown) to form a phase-contrast microscopic image of the lymphocytes. When viewed through the phase-contrast microscope, the image of positive lymphocyte is dark and plain circular or elliptical in shape. Its size is relatively large. In contrast, the image of negative lymphocyte is relatively small and bears a bright halo. Many of the negative lymphocyte images are annular in shape but some are non-annular.

FIG. 2 shows typical relation curves between the number of lymphocytes and the size thereof, of which the curve 4A shows the distribution of positive lymphocytes and the curve 4B does that of the non-annular negative lymphocytes. These are plotted with the number of lymphocytes as the axis of ordinate and the size of lymphocytes as the axis of abscissa. As seen from FIG. 2, the distribution 4A of positive lymphcytes and the distribution 4B of non-annular negative lymphocytes are not fully separative but partly overlapped each other.

In an embodiment of the present invention shown in FIG. 3, the above wells 3 of a microtest plate are examined one by one through a phase-contrast microscope 7. The microscopic image obtained by the phase-contrast microscope 7 is transformed into picture signals (electric video signals) by an image pick-up unit 8 such as a raster scan type TV camera. FIG. 4A is a schematic illustration of a positive lymphocyte image 4a and an annular negative lymphocyte image 4b. By scanning these different lymphocyte images along the centers thereof there is produced a picture signal 8A having a wave form corresponding to the images 4a and 4b as shown in FIG. 4B.

A timing pulse generator 9 receives from the image pick-up unit 8 a synchronizing signal 8B which is in synchronism with the scanning, and generates a clock pulse by which the operational consistency of the apparatus is maintained as a whole.

The picuture signal 8A is introduced into a binarizing threshold generator 10 which, then, generates three different kinds of binarizing threshold signals, namely signals 10A, 10B and 10C. These binarizing threshold signals 10A, 10B and 10C are set in signal level with respect to the picture signal 8A as shown in FIG. 4B. The level of signal 10A is so determined as to keep best the features of geometrical shapes of positive and negative lymphocyte images, the level of threshold signal 10B is so determined as to keep the features of dark portions of the image such as thickly dyed portions of lymphocyte and the threshold signal 10C is set to a level most suitable for keeping the features of light portions of the image such as haloes around negative lymphocytes. Alternatively, these binarizing threshold signals may be floating binarizing threshold signals produced in time series on the basis of a certain definite range of amplitude of the picture image.

Of three threshold signals the signal 10A is introduced into a binarizing circuit 11 which produces a binary picture signal 11A. As shown in FIG. 4C, the output 11A becomes logic "1" when the level of the picture signal 8A becomes lower than the threshold 10A. Similarly, threshold signal 10B is introduced into a binarizing circuit 12 which has a binary picture signal output 12A which is "1" when the level of the picture signal 8A is lower than the threshold 10B. Binarizing circuit 13 receives the threshold signal 10C and puts out a binary picture signal 13A which becomes "1" when the level of the picture signal 8A becomes higher than the threshold 10C.

In the manner described above, a picture signal 8A is branched into three binary picture image lines through binarizing circuits 11, 12 and 13. Hereinafter, description of the after-processing of signal will be made individually for every line.

(1) Binary picture signal 11A:

This output signal 11A from the binarizing circuit 11 is introduced into a window circuit (for parallel local operation) 14. The function of window circuit 14 is to put out a binary picture signal for a determined area of the original image (microscopic image) at the same time and in parallel. To this end, the window circuit 14 receives sequentially binary picture signal 11A generated in time series and stores the signal in a memory. From among the stored signal the window circuit puts out those signals corresponding to a determined area of the original image at once in parallel. For the purpose of explanation this operation of the window circuit 14 is described in detail with reference to the case of a 5 by 5 window (a square area in the original image containing 5×5 picture elements).

In FIG. 5, the window circuit 14 comprises serial input-parallel output type shift registers 14a to 14e each having storage bits corresponding to one scanning line amount of picture signal. Each the shift register issues parallel output of five picture elements (abridged as pixel for every scanning line. Outputs $S_{00}$–$S_{44}$ from the shift registers 14a–14e are 25 lines in total and include logic values "1" and "0" for the 5 by 5 window with a relative phase relation on the image as shown in FIG. 6. Thus, the shift registers 14a–14e generate parallel outputs $S_{00}$–$S_{44}$ while receiving serial binary picture signals 11A in time series from the binarizing circuit 11. This may be considered to be equivalent in effect to that the image is rasterscanned by the square area shown in FIG. 6.

Outputs from the shift registers 14a–14e are all together represented by 14A. The output 14A is applied to pattern matching circuits 15, 16 and 17. The first pattern matching circuit 15 has a sufficiently large template pattern enough to detect those lymphocytes larger than the size $G_1$ in FIG. 2. Examples of such relatively large template pattern are shown in FIGS. 7A and 7B. the template pattern shown in FIG. 7A is such pattern wherein pixels $S_{00}$, $S_{04}$, $S_{40}$ and $S_{44}$ at the four corners of the above mentioned 5 by 5 window are either logic "1" or "0" and all of the remaining twenty one pixels are "1". The template pattern shown in FIG. 7B is such one wherein four pixels $S_{00}$, $S_{34}$, $S_{43}$ and $S_{44}$ are either "0" or "1" and the remaining pixels are all "1". The pattern matching circuit issues an output 15A of logic "1" only when the outputs $S_{00}$–$S_{44}$ for 5×5 pixels from the window circuit 14 satisfy the above template pattern.

The second pattern metching circuit 16 has a template pattern smaller than that of the above matching circuit 15 so as to detect non-annular lymphocytes larger than the size $G_2$ in FIG. 2. As shown in FIG. 8, this relatively small template pattern is such pattern wherein 4×4 pixels are all logic "1". Therefore, the second pattern matching circuit 16 issues an output 16A of logic "1" only when the outputs the portion of 4×4 pixels from the window circuit 14 satisfy the template pattern shown in FIG. 8.

The third pattern matching circuit 17 has a ring template pattern as shown in FIG. 9. The template pattern shown in FIG. 9 is such pattern wherein at least one of the central pixels $S_{11}$, $S_{12}$, $S_{21}$ and $S_{22}$ in 4×4 pixels $S_{00}$–$S_{33}$ is logic "0" and a larger number of pixels of the remaining surrounding pixels than a predetermined number are logic "1". Herein, the condition "a predetermined number" means that the ring pattern is not always required to be a completely closed ring. The pattern matching circuit 17 issues an output 17A of logic "1" only when the outputs from the window circuit 14 satisfy the ring template pattern. In other words, the output 17a is issued when an output indicative of annular negative lymphocyte is obtained from the window circuit 14.

Outputs 15A, 16A and 17A from the pattern matching circuits 15, 16 and 17 are introduced into end point detectors 18, 19 and 20 respectively. These end point detectors generate each one logic "1" output per one lymphocyte detected from the output 15A, 16A, 17A. The end point detectors 18, 19 and 20 are provided for the following reason:

In matching pattern using template patterns as described above, there arises a problem. In the case of a pattern lymphocytein an image larger than the template pattern, logic output informing that the given condition for matching is satisfied will be issued a plural number of times within the pattern. Therefore, if the number of issued logic outputs is counted by a counter, then the value of counts will be inconveniently over the real number of existing lymphocytes. End point detectors 18, 19 and 20 are provide to solve such problem. Outputs 18A, 19A and 20A from the end point detectors are introduced into counters 24, 25 and 26 through AND gates 21, 22 and 23 respectively. To the other input terminal of each the AND gate is applied a mask signal from a mask signal generator 27 of which description will be made in detail hereinafter. On this way, The counter 24 counts the number of those lymphocytes which are on-annular in shape and larger than $G_1$ in size. The second counter 25 counts the number of those lymphocytes which are non-annular in shape and larger than $G_2$ in size and the third counter 26 counts the number of annular negative lymphocytes. Based on data about the size of lymphocytes given by the counters 24 and 25 and data about annular shape given by the counter 26, the positivity of HLA can be primarily determined with some accuracy. However, in the shown embodiment, the following data processing is carried out to further improve the accuracy.

(2) Binary picture signal 12A:

As previously noted, positive lymphocyte is relatively large in size and dyes well with eosin, which renders a dark picture signal. Therefore, the positive lymphocyte can be identified by its two features, that is, large size in geometrical feature and dark in density feature. Signal containing both of these features may be regarded as a signal of positive lymphocyte with higher probability. For this reason, in the processing line of the binary picture signal there is provided an AND gate 29.

Figure 10:
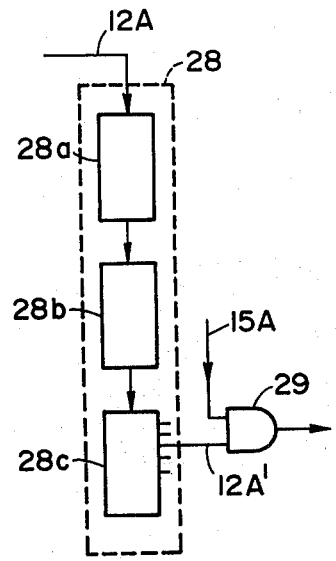
FIG. 10 is a block diagram showing a concrete form of delay circuit.

The binary picture signal 12A is introduced into a delay circuit 28 from the binarization circuit 12 to form a delayed signal 12A'. At the AND gate 29, logic product of the delayed output 12A' and the output 15A from the pattern matching circuit 15 is found. The function of delay circuit 28 is to synchronize the logic output from the binarization circuit 12 with the logic output from the pattern matching circuit 15. Since picture signal in an amount of five scanning lines is required until all of the outputs fully come out from the window circuit 14 in FIG. 5, the above synchronization becomes necessary. As shown in FIG. 10, the delay circuit 28 comprises three serial input-parallel output type shift registers 28a, 28b and 28c each having storage bits corresponding to one scanning line picture signal so that the delayed output 12A' and the output 15A from the pattern matching circuit 15 can be made correspond each other at the position of the pixel S22.

As previously noted, in case that a lymphocyte is sufficiently larger than the template pattern of the pattern matching circuit 15, said circuit 15 issues the output relating to the same lymphocyte a plural number of times and therefore AND gate 29 also issues the output a plural number of times for said one and same lymphocyte. To solve this problem and to obtain correctly one logic output per one lymphocyte, there is provided an end point detector 30 also in this processing line. Namely, output 30A from the end point detector 30 is applied to a counter 32 through AND gate 31. The counter 32 counts the number of the outputs 30A from the end point detector as the number of existing positive lymphocytes.

(3) Binary picture signal 13A:

This binary picture signal 13A is an output signal from the binarization circuit 13 which binarizes the light portion of a picture signal 8A corresponding to halo of negative lymphocyte by means of the threshold 10C as shown in FIG. 4E. The binary picture signal 13A is introduced into a window circuit 33 for picking out a 5 by 5 window. The window circuit 33 is entirely the same as that shown in FIG. 5 in structure. Output from the window circuit 33 is put into a pattern matching circuit 34 which has a template pattern for detecting halo. The template pattern is a relatively large ring pattern. For example, referring to FIG. 6, the template pattern may be such one wherein pixels S01–S03, S10, S20, S30, S14, S24, S34, S41–S43 are all logic "1" and pixels S11–S13, S21–S23, S31–S33 are all logic "0". The pattern matching circuit 34 generates a logic output 34A, that is, logic "1" only when the output 13A satisfies the template pattern. For the same reason as above, the logic output 34A is put into an end point detector 35 which issues one logic output 35A per one negative lymphocyte. The output 35A is then applied to a counter 37 through AND gate 36. The counter 37 counts the number of the outputs 35A as the number of existing negative lymphocytes.

This third line 13, 33–37 is provided to detect negative lymphocytes relying upon halo in parallel with the first 11, 14, 17, 20, 23, 26 line including the pattern matching circuit 17. In the first line, negative lymphocytes are detected relying upon the ring pattern of the pattern matching circuit 17. The third line plays a subsidiary role in detecting negative lymphocyte relative to the first line including the pattern matching circuit 17.

After processing picture signals in the above described three lines there are obtained the following five defferent data;

From counter 24: data about the number of those lymphocytes which are non-annular in shape and larger than $G_1$ in FIG. 2 in size, namely those lymphocytes which may be regarded as positive lymphocytes with high probability.

From counter 25: data about the number of those lymphocytes which are non-annular in shape and larger than $G_2$ in size.

From counter 26: data about the number of annular negative lymphocytes.

From counter 32: data about the number of typical positive lymphocytes which are large in size and dyes well.

From counter 37: data about the number of haloes.

Figure 11:
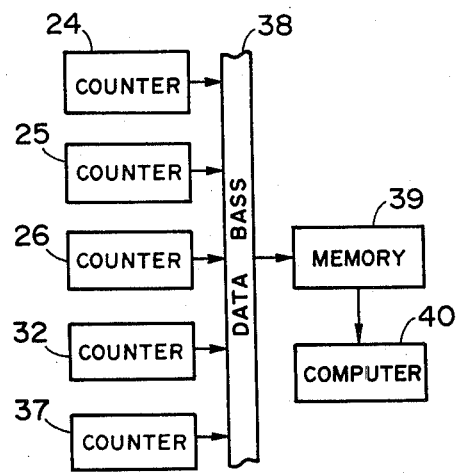
FIG. 11 is a block diagram of a positivity determining circuit.

The above processing is repeated as many times as the number of wells provided in the microtest plate. Count values at the counters 24, 25, 26, 32, 37 obtained from every well are delivered to a memory 39 through a data bus 38 as shown in FIG. 11 and stored therein in the locations alloted for the respective well. The stored values are synthetically judged by a computer 40 to determine the positivity for every well.

The positivity can be determined based upon the above count values in the following manner:

Assuming that the values obtained from the counters 24, 25, 26, 32 and 37 are 24N, 25N, 26N, 32N and 37N, computing is made at first to know the difference between 25N and 24N, (25N−24N). The found difference is the number of those lymphocytes which are non-annular in shape and can be regarded as negative lymphocytes with high probability. On the other hand, 24N is the number of those lymphocytes which are probably positive lymphocytes. Therefore, the positivity can be determined from the ratio of 24N/(25N−24N) with a considerably high reliability.

The accuracy in determining the positivity can be further improved by employing the following procedure:

At first the total number of lymphocytes is found as (25N+26N). Then, calculations are carried out to known the ratio of the number of large size lymphocytes to the total number, that is, 24N/(25N+26N), the ratio of the number of haloes to the total number, that is, 37N/(25N+26N) and the ratio of the number of annular negative lymphocytes to the total number, that is, 26N/(25N+26N). These ratios and the above ratio 24 N/(25N−24N) are synthetically judged to determine the positivity.

Figure 12:
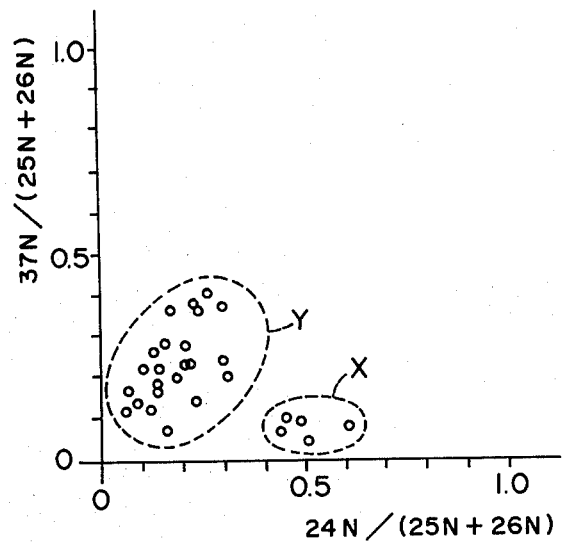
FIG. 12 is a graph in which data of the respective wells are plotted with the data of larger lymphocyte as the axis of ordinate and the data of halo as the axis of abscissa.

These ratios found by above calculations may be fisually displayed to determine the positivity for every well. FIG. 12 shows an example of such displayed graph in which above-mentioned ratios for every well are plotted with the ratio 37N/(25N+26N) as the axis of ordinate and the ratio 24N/(25N+26N) as the axis of abscissa. From the figure, it is observed that the wells contained in the group X are high in the ratio of the number of large lymphocytes to the total number but low in the ratio of the number of haloes to the total number. On the contrary, as for the wells contained in the group Y it is observed that the former ratio is low but the latter ratio is high. From these visual observations, the wells in the group X can be judged to be positive and those in the group Y to be negative with high probability.

Hereafter, the respective components of the apparatus shown in FIG. 3 will be described in detail.

FIG. 13 shows a concrete circuit form including the pattern matching circuits 15, 16, 17 and end point detectors 18, 19, 20. Since circuits 15, 16, 17 are all the same in structure, herein the pattern matching circuit 15 is described representatively. The circuit 15 is composed of an AND gate 15a which receives from the window circuit 14 parallel outputs 14A corresponding to the pixels S01–S03, S10–S14, S20–S24, S30–S34, S41–S43. With this arrangement it can be detected whether the condition of the template pattern shown in FIG. 7A is satisfied or not. To form the circuit for carrying out the detection with the template pattern shown in FIG. 7B, the output 14A corresponding to the pixels S34 and S43 is replaced by that corresponding to the pixels S04 and S40. If it is desired to detect whether at least either one of the two conditions is satisfied or not, then separate AND gates are provided and the respective outputs from the AND gates are applied to an OR gate.

Like the circuit 15, the pattern matching circuits 16 and 17 are composed of AND gates 16a and 17a respectively.

The end point detector 18 comprises a delay circuit 18a and a comparator 18b. The delay circuit 18a is so formed as to delay the output 15A by a delay time corresponding to one scanning line. The comparator 18b makes a comparison in time series between the output 15A and the output from the delay circuit 18a to check the connection of the former with the latter. When the connection is broken, the comparator issues a logic output "1". This makes it possible to count the number of lymphocyte patterns correctly one by one even when the lymphocyte pattern in an image is larger than the template pattern. The output "1" from the comparator is applied to the counter 24 at the next step for counting the number of the outputs. Thus, the number of lymphocyte patterns existing in the image can be found out.

Other end point detectors 19 and 20 have the same structure as that of the above described end point detector 18.

Hereafter, function and arrangement of the mask signal generator 27 will be described in detail with reference to the related drawings.

At first the reason why the mask signal generator is necessary will be described. FIG. 14 is a microscopic image of a well 3 as viewed from the bottom side. The edge 3a of the well 3 defines a sample area wherein lymphocytes 4 are observed. Hereby it should be noted that there is a distinct difference in density level between the image of the sample area (lymphocytes) and the image of the well side wall 3b. The microscopic image is raster scanned to form a picture signal 8A. As an example, FIG. 15 shows a wave form of such picture signal 8A as obtained by scanning along the line segment x-y shown in FIG. 14. As seen from the wave form in FIG. 15, the signal level varies with proceeding of scanning. Signal area $S_1$ is at a level corresponding to the side wall 3b of the well 3. Area $S_2$ has a level corresponding to the well edge 3a. Next to the area $S_2$ there appears signal area $S_3$ the level of which corresponds to the sample area within the well. The signal area $S_3$ is followed by areas $S_2'$ and $S_1'$ corresponding to the well edge and the well side wall. As readily understood, the signal portions $S_1$ and $S_1'$ corresponding to the well side wall and the signal portions $S_2$ and $S_2'$ corresponding to the well edge must be excluded from the picture signal. Otherwise these signal portions will have adverse effect on the counted number by the counters 24-26, 32 and 37. Masking signals are necessary to extract from the picture signal only the signal portion $S_3$ corresponding to the sample area within the well.

FIG. 16 shows a circuit for generating such mask signal and FIG. 17 shows a timing chart of the circuit.

In FIG. 16, a TV camera 8 which may be, for example, of sequential scanning type, produces a picture signal 8A. The picture signal 8A is binarized by a binarization circuit 100. As shown in FIGS. 17A and 17B, the threshold $T_1$ to the binarization circuit 100 is preset in such manner that the signal portions $S_1$ and $S_1'$ having the level corresponding to the well side wall are rendered logic "0" and the signal portions having a level higher than said level are rendered logic "1". Binary output signal 100A from the binarization circuit 100 is applied to digital delay circuits 101 and 102. Let the time required for one scanning by the TV camera 8 be 1H. Then, the digital delay circuit 101 delays the binary output 100A by a delay time, (1H−Δ). This delayed output is referred to as 101A. Similarly, as shown in FIG. 17D, the delay circuit 102 produces a delayed output 102A which was delayed by a delay time, (1H−Δ2) relative to the output 100A. Times Δ1 and Δ2 are selected optionally as required and may be equal to each other or different from each other. AND gate 103 receives the two delayed outputs 101A and 102A and issues a mask signal 103A (FIG. 17E). This mask signal 103A is an output as obtained by delaying the rise time of the binary output 100A by Δ2 and advancing the fall time thereof by Δ1. This mask signal 103A is introduced into AND gates 21–23, 31 and 36 shown in FIG. 3. Therefore, by selecting, as the delay times Δ1 and Δ2, a time longer than the generation time of the edge signals $S_2$ and $S_2'$ such mask signal can be obtained which well corresponds to the sample area enclosed by chain-dotted line 4C at the inside of the well edge 3a in FIG. 14. Consequently, from the counters 24-26, 32 and 37 in FIG. 3 there are obtained count values free of undesirable information derived from the well side wall and well edge portion.

As a modification of the above embodiment, it is also possible to make the masking signal act on the picture signal 8A itself so as to preliminarily exclude the undesirable signal components $S_1$, $S_1'$ and $S_2$, $S_2'$ from the picture signal. A pure picture signal thus obtained is used to detect the lymphocytes present within the well. This modification is described also with reference to FIG. 16.

In FIG. 16, a picture signal from the camera 8 is applied to an analogue delay circuit 104 which delays the signal by one scanning time, 1H. The delayed picture signal from the delay circuit 104 is applied to an inhibit circuit 105 which is receiving also the mask signal 103A as a control input. The inhibit circuit 105 allows the delayed picture signal to pass through toward the processing circuits 10–13 only when the mask signal 103A is "1". All the time other than it, the inhibit circuit 105 inhibits the signal from passing through.

In the shown embodiment, the mask signal formed from the picture signal obtained by the scanning of the segment x-y acts as a masking signal to the picture signal obtained by the same scanning. In other words, there occurs so-called real time masking. However, in the embodiment shown in FIG. 16, the picture signal 8A may be applied directly to the inhibit circuit 105 without passing through the delay circuit 104. Considering two vertically adjacent scanning lines in raster scanning, there is observed substantially no change in image pattern from one scanning line to the next one. Therefore, the mask signal derived from the picture signal 8A can be used for the next picture signal delayed from the picture signal 8A by one scanning line without any problem.

Delay circuits 101 and 102 mentioned above may be formed of shift registers in a simple manner. Also, delay times to be set for the delay circuits 101, 102 and 103 may be $(nH-\Delta 1)$, $(nH+\Delta 2)$ and nH wherein n is an integer.

In FIG. 1B, reference numeral 106 indicates an air bubble generated in a well 3. Presence of such bubble 106 within the well results in degraded image in this area. Therefore, in this case it can be no longer expected that good result may obtained by image processing. It is required to eliminate adverse effect by such bubble present in the well in addition to the adverse effect by the well edge portion described above. Hereafter, an embodiment of circuit for eliminating such adverse effect will be described with reference to FIGS. 18 to 21.

FIG. 18 shows an image of well in which an undesirable bubble 106 is present. Since the image of such bubble is very bright, the picture signal obtained by scanning the well image by scanning line x-y contains a very high level portion $S_4$ corresponding to the bubble area as shown in FIG. 19.

In the circuit shown in FIG. 20, the picture signal 8A containing the bubble signal portion $S_4$ is introduced into a binarization circuit 106 to binarized the signal. As shown in FIG. 21A, the binarization circuit 102 has a sufficiently high level threshold $T_2$ enough to detect the bubble area $S_4$ only. Therefore, as shown in FIG. 21B, the output 107A from an inverter 107 becomes "0" at the bubble area $S_4$ and "1" at the remaining area. A second binarization circuit 108 has a second threshold $T_1$ and generates an output 108A as shown in FIG. 21C. This output 108A has a signal 108a of "0" resulting from the image of lymphocyte. AND gate 109 makes up an output 109A (FIG. 21D) from the two outputs 107A and 108A. A monostable multivibrator 110 is triggered by the negative edge of the output 109A to generate a pulse output 110A of "1" corresponding to the lymphocyte signal 108a of the output 108A (FIG. 21E). A delay circuit 111 is provided to delay the output 109A by a delay time which is a little longer than the propagation delay time of the multivibrator 110. Outputs 110A and 111A are applied to OR gate 112 which forms an output 112A as obtained by excluding the lymphocyte signal 109a from the corresponding output 109A. From the output 112A there is obtained a mask signal 115A as shown in FIG. 21J through a pair of delay circuits 113 and 114 and an AND gate 115 which are entirely the same as delay circuits 101, 102 and AND gate 103 shown in FIG. 16 in function as well as arrangement.

The purpose for which the embodiment shown in FIG. 20 has been used can be attained also by another embodiment as shown in FIG. 22. Timing chart thereof is shown in FIG. 23.

Figure 23C:
Figure 23D:
Figure 23E:
Figure 23F:
Figure 23G:
Figure 23H:
Figure 23I:
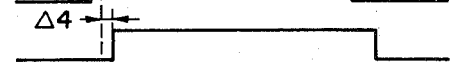
Figure 23J:
Figure 23K:

In the circuit shown in FIG. 22, a picture signal 8A is introduced at first into a low-pass filter 116 to filter off the signal component corresponding to lymphocyte. A filtered signal 8A' from the low-pass filter is applied to binarization circuits 117 and 118. The binarization circuit 117 has a threshold $T_2$ to form a binary signal 117A (FIG. 23C) whereas the other binarization circuit 118 has a threshold $T_1$ to form a binary signal 118A (FIG. 23D). The binary signal 117A is put into delay circuits 119 and 120. The delay circuit 119 generates a delayed output 119A with a delay time, $1H-\Delta 1$ and the other delay circuit 120 generates a delayed output 120A with a delay time, $1H-\Delta 2$ from the two delayed outputs 119A and 120A an AND output 121A is produced by an AND gate 121. On the other hand, the binary signal 118A is introduced into two delay circuits 122 and 123 which generate a delayed output 122A with a delay time, $1H-\Delta 3$ and a delayed output 123A with a delay time, $1H-\Delta 4$ respectively. These delayed outputs 122A and 123A are applied to an AND gate 124 which issues an AND output 124A of 11A and 123A. Finally, AND gate 125 makes up an AND output 125A from the AND outputs 121A and 124A and the AND output 125A is issued as a mask signal.

As previously described, annular negative lymphocytes are detected by the pattern matching circuit 17 shown in FIG. 3. A further detailed description of the pattern matching circuit 17 will be made hereinafter.

An image of annular negative lymphocyte is binarized by the binarization circuit 11 as described above. FIG. 24A shows a general form of such binarized image of annular negative lymphocyte. However, this form of the binary image is sometimes deformed by eccentricity of the central light portion of a negative lymphocyte caused by optical distortion of the negative lymphocyte itself or an adjustment error of the phase-contrast optical system. FIG. 24B shows an example of the binary image of such deformed annular negative lymphocyte image wherein a portion of the ring is broken. Therefore, in detecting annular negative lymphocytes it is required to detect not only a complete ring pattern as shown in FIG. 24A but also an incomplete ring pattern as shown in FIG. 24B. However, if such incomplete patterns in which a portion of the ring is broken are detected as negative lymphocytes without any restirction, there may arise some problem. For example, in case that lymphocytes exist close together as shown in FIGS. 25A–25D, area around the adjacent lymphocytes may be detected as a negative lymphocyte erroneously. Possibility of such erroneous detection has to be minimized. Some examples of template pattern which enables to detect annular negative lymphocytes with higher reliability are described hereinafter with reference to FIGS. 26 to 28. While in the embodiment shown in FIG. 3 there has been used a template pattern of negative lymphocyte having 4×4 pixels as shown in FIG. 9, the following examples of template pattern are shown to be of 5×5 pixels assuming that the negative lymphocytes are larger than those in FIG. 3 embodiment.

FIG. 26 shows 5×5 pixels of which the center one is denoted by C, eight pixels directly surrounding the center one by H0–H7, pixels at four corners by A and the remaining twelve peripheral pixels by S0–S11. For the purpose of illustration, the center pixel C and the surrounding pixels H are together referred to as central pixels and the corner pixels A and the peripheral pixels S are together referred to as circumferential pixels. A template pattern for detecting annular negative lymphocytes has to satisfy the following requirements (1), (2) and (3):

(1) Among the central pixels C, H at least the center pixel C should be logic "0".

(2) A completely closed ring should exist around the center pixel C, said closed ring being formed of connected pixels of logic "1" as shown in FIGS. 27A–27C; or an incomplete ring, that is, a ring which is broken at only one portion thereof should exist around the center pixel C. Examples of the incomplete ring include patterns shown in FIGS. 28A and 28B and those as obtained by rotating the patterns 90°, 180° or 270°. Here, it should be noted that while in FIG. 9 hatched pixels have been of logic "0", hatched pixels in FIGS. 27 and 28 are of logic "1".

(3) In case of the incomplete ring, the broken portion should be smaller than the diameter of the ring.

Preferably, such additional requirement is added to the above three requirements that at least the majority of the central pixels C, H0–H7 should be logic "0". Since the ring is circular, the pixels A may be "0" or "1". As seen from FIGS. 27 and 28, the term "connected pixels" means that one pixel and another pixel lying next to it in any direction of upward, downward, leftward, rightward and diagonal are connected each other.

Figure 29:
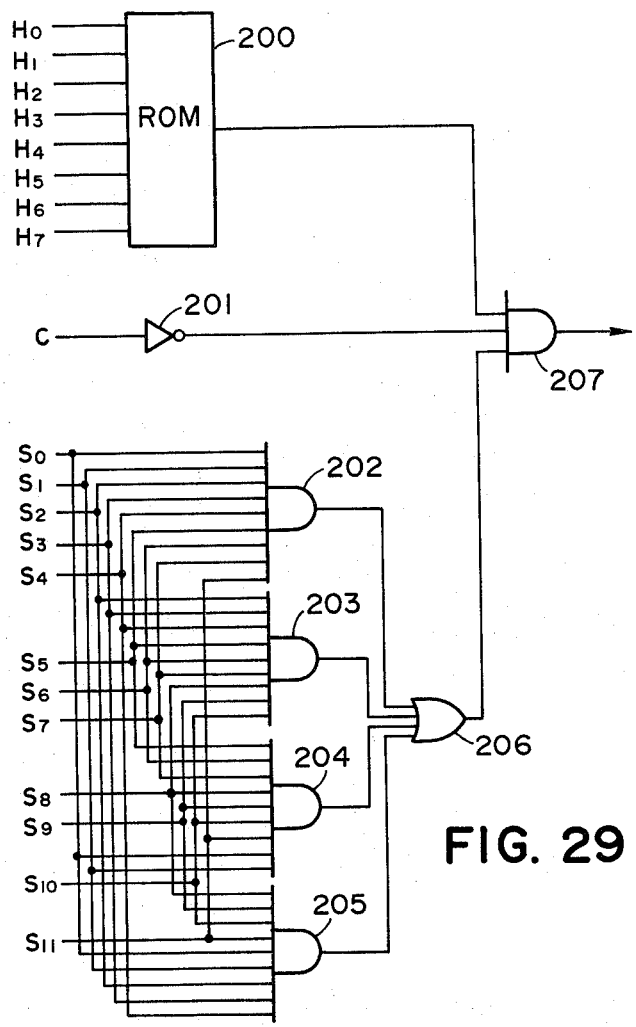
FIG. 29 shows an embodiment of the pattern metching circuit for detecting annular lymphocytes.

FIG. 29 shows an embodiment of the pattern matching circuit having template patterns as shown in FIG. 28A and obtained by rotating it 90°, 180° and 270°.

ROM 200 receives eight outputs from the window circuit 14 in FIG. 3 corresponding to the center surrounding pixels H0–H7 respectively. ROM 200 issues an output, logic "1" when the majority of the inputs to it, for example not less than 5 are logic "0".

Inverter 201 inverts the binary output corresponding to the center pixel C. AND gate 202 receives the binary outputs corresponding to the circumferential pixels S0–S7 and S11 and puts out an AND thereof.

AND gate 203 issues an AND of pixels S2–S10, AND gate 204 issues an AND of pixels S5–S11, S0 and S1 and AND gate 205 issues an AND of pixels S8–S11, S0 and S1–S4.

As previously noted, in this embodiment, pixels A at four corners are not used as data.

OR gate 206 issues an OR of the outputs from the above AND gates 202–205. AND gate 207 issues an AND of the outputs from ROM 200, inverter 201 and OR gate 206. With this arrangement of the circuit, therefore, the AND gate has logic "1" at its output only when the majority of the center surrounding pixels H0–H7 are logic "0", the center pixel C is "0" and any of the pixel groups, (S0–S7, S11), (S2–S10), (S5–S11, S0, S1) and (S8–S11, S0, S1–S4) is "1". These cases correspond to the incomplete ring pattern shown in FIG. 28A and those incomplete patterns as obtained by rotating the pattern shown in FIG. 28A by 90°, 180° and 270°. Thus, it is made possible to detect the presence of any incomplete ring pattern.

Three requirements (1) to (3) described above may be generalized as follows:

(a) The center pixel and not less than one of the central pixels in a window should have first logic value;

(b) A completely closed ring of second logic value or an incomplete ring of second logic value wherein the ring is broken at only one portion thereof would be present at the circumferential part of the window; and (c) In the case of incomplete ring, the size of its broken portion should be smaller than the diameter of the ring.

A detailed description of circuit 10 for generating threshold for binarization and circuit 11 for binarization shown in FIG. 3 will be made hereinunder with reference to FIGS. 30 through 36.

Figure 30:
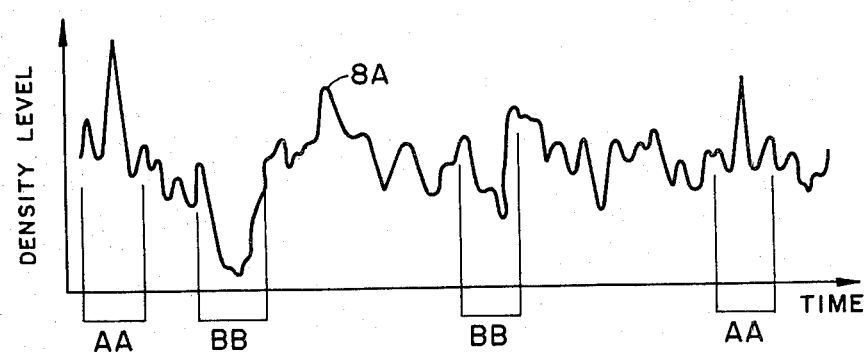
FIG. 30 shows a wave form of an actual picture signal.

As shown in FIG. 30, the real wave form of a picture signal 8A coming from the TV camera 8 varies within a wide range of density level with time. In the wave form curve, the area AA corresponds to image of annular negative lymphocyte and BB to image of positive lymphocyte. This picture signal 8A is transformed into a binary picture signal such as the signal 11 shown in FIG. 4C using a threshold signal 10A. In this case, the threshold signal 10A should be not a fixed value but a floating threshold variable depending upon the picture signal 8A.

Figure 31:
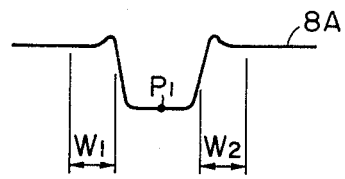
FIG. 31 shows a wave form of a picture signal representative of positive lymphocyte.
Figure 32:
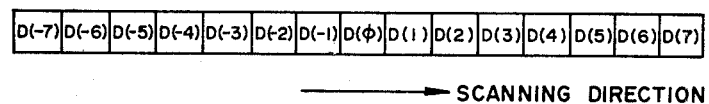
FIG. 32 shows a pixel along one scanning line.

For the above reason, it is advisable that the threshold used for detecting positive lymphcyte be determined in the following manner:

FIG. 31 schematically shows a curve portion of the picture signal 8A corresponding to a positive lymphocyte whose center is designated by $P_1$. $W_1$ and $W_2$ designate predetermined areas at both outer sides of the center. As the threshold for the picture signal of the center $P_1$ of a positive lymphocyte, a means value of picture signals at the two areas $W_1$ and $W_2$ can be used advantageously. More concretely, if pixels of a positive lymphocyte are denoted by symbols as shown in FIG. 32, then the threshold $T_p$ of the pixel $D(0)$ can be determined by the average value of $D(4)$ to $D(7)$ and $D(-4)$ to $D(-7)$. Namely, $$T_p = \frac{\{D(-7)+D(-6)+D(-5)+D(-4)+D(4)+D(5)+D(6)+D(7)\}}{8 - D_c}$$

wherein $D_c$ is a constant which is experimentally determined to eliminate the effect of white color noise contained in the picture signal.

Figure 33:
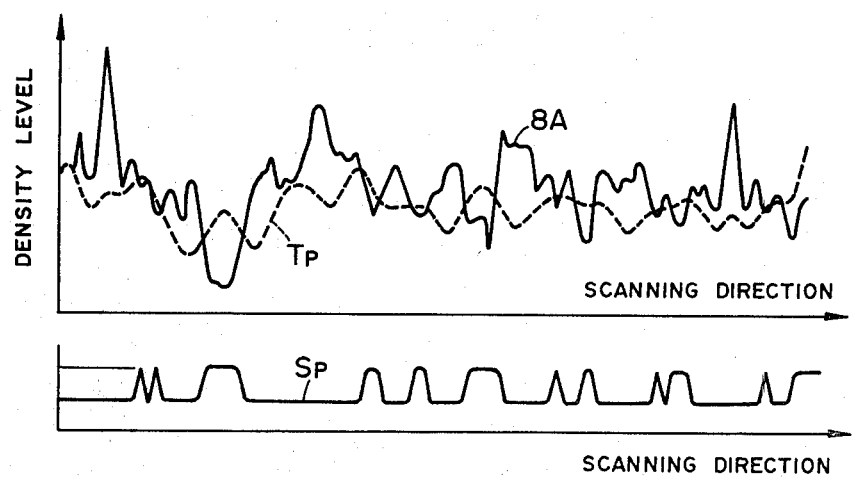
FIG. 33 is a wave form chart showing a picture signal, a threshold signal and a binarized signal together.

FIG. 33 shows the wave form of the threshold signal $T_p$ obtained in this manner and the binary picture signal $S_p$ formed by using the threshold.

As seen from FIG. 33, the threshold $T_p$ is able to faithfully binarize the picture signal as far as positive lymphocytes concern. But the picture signal of negative lymphocyte can not be binarized by it at all. This is because the threshold gently follows the picture signal 8A. While it is suitable for binarizing the picture signal of positive lymphocyte, it can not follow minute change of the picture signal as in the case of negative lymphocyte.

Figure 34:
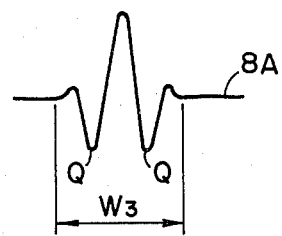
FIG. 34 schematically shows a wave form of a picture signal representative of annular negative lymphocyte.

Since the picture signal of negative lymphocyte varies relatively minutely, it is required to use another mean value for determining the threshold for negative lymphocyte. For example, when a threshold useful for faithfully binarizing two dark parts Q as shown in FIG. 34 is required to use a mean value of a wider pixel area nearly equal to the diameter $W_3$ of a negative lymphocyte. In general, a negative lymphocyte detecting threshold TN for a pixel D(0) is determined by:

$$TN = \frac{\{D(-4)+D(-3)+D(-2)+D(2)+D(3)+D(4)+2\times D(0)\}}{8 - Dc}$$

Figure 35:
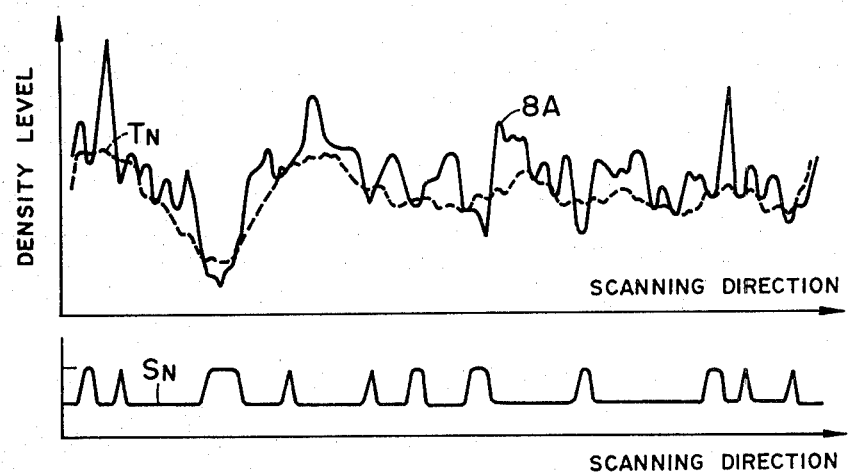
FIG. 35 is a wave form chart similar to FIG. 33.
Figure 36:
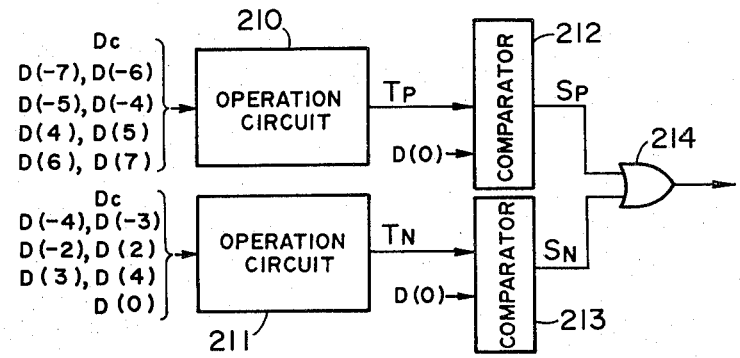
FIG. 36 is a block diagram of an embodiment of the binarizing threshold generator and binarizing circuit.

FIG. 35 shows the picture signal 8A, the threshold TN obtained in this manner and the binary signal SN formed using the threshold. From FIG. 35 it is seen that two dark parts of a negative lymphocyte are faithfully binarized and that the followability of the threshold is so high that at the dark part of a positive lymphocyte the level of the threshold also lowers and therefore the dark part of a positive lymphocyte is also subjected to a faithful binarization by this threshold undesirably. This means that in case that positive lymphocytes and negative lymphocytes are present at the same time, use of only one of the two thresholds Tp and TN sometimes leads to an incorrect binarization of such picture signal. Therefore, in such cases, it is required to make up a logical sum of the result of binarization by Tp and the result of binarization by TN and to use the logical sum as a final result of binarization. This may be attained, for example, by employing a circuit as shown in FIG. 36.

A first operation circuit 210 carries out a computation to find out Tp from picture signals relating to pixels D(−7), D(−6), D(−5), D(−4), D(4), D(5), D(6), D(7) and a above mentioned constant signal Dc. Similarly, a second operation circuit 211 carries out a computation to find out TN from picture signals relating to pixels D(−4), D(−3), D(−2), D(2), D(3), D(4), D(0) and a constant signal Dc. A first comparator 212 compares the picture signal of pixel D(0) with the threshold Tp and issues logic "1" when Tp>D(0). A second comparator 213 compares the picture signal of pixel D(0) with the threshold TN and issues logic "1" when TN>D(0). Two outputs Sp and SN from the comparators 212 and 213 are applied to OR gate 214 which makes up logical sum of Sp and SN.

While the present invention has been particularly shown and described with reference to preferred embodiments thereof, it will be understood by those skilled in the art that the foregoing and other changes in form and details can be made therein without departing from the spirit and scope of the invention.

We claim:

1. An automatic HLA typing apparatus comprising:

a phase-contrast microscope for forming an optical image of a sample containing lymphocytes;

image pick-up means for transforming said optical image into a binary picture signal to transform the images of lymphocytes into binary picture patterns wherein the binary picture pattern indicative of the image of a positive lymphocyte is a non-annular in shape and relatively large in size whereas the binary picture pattern indicative of the image of a negative lymphocyte is annular or non-annular in shape and relatively small in size;

first detection means for receiving said binary picture signal and detecting from said signal those binary picture patterns which are non-annular and larger than a first determined size;

first counter means for counting the number of binary picture patterns detected by said first detection means;

second detection means for receiving said binary picture signal and detecting from said signal those binary picture patterns which are non-annular and larger than a second determined size that is smaller than said first determined size; and second counter means for counting the number of binary picture patterns detected by said second detection means.

* * * * *